US012766326B2

(12) United States Patent
Burnam et al.

(10) Patent No.: US 12,766,326 B2
(45) Date of Patent: Oct. 20, 2026

(54) SYSTEMS AND METHODS FOR STATE MACHINE SELECTION FOR PACING

(71) Applicant: BaroPace, Inc., Ashland, OR (US)

(72) Inventors: Michael Burnam, Ashland, OR (US); Eli Gang, Los Angeles, CA (US); Srikanth Jadcherla, Frisco, TX (US)

(73) Assignee: BaroPace, Inc., Ashland, OR (US)

( * ) Notice: Subject to any disclaimer, the term of this patent is extended or adjusted under 35 U.S.C. 154(b) by 219 days.

(21) Appl. No.: 18/840,812

(22) PCT Filed: Feb. 23, 2023

(86) PCT No.: PCT/US2023/063143
§ 371 (c)(1),
(2) Date: Aug. 22, 2024

(87) PCT Pub. No.: WO2023/164560
PCT Pub. Date: Aug. 31, 2023

(65) Prior Publication Data
US 2025/0174347 A1 May 29, 2025

Related U.S. Application Data

(60) Provisional application No. 63/268,554, filed on Feb. 25, 2022.

(30) Foreign Application Priority Data

May 17, 2022 (IN) ............................. 202244028218

(51) Int. Cl.
*A61N 1/365* (2006.01)
*A61N 1/37* (2006.01)
*A61N 1/372* (2006.01)

(52) U.S. Cl.
CPC ..... *A61N 1/36564* (2013.01); *A61N 1/36542* (2013.01); *A61N 1/36585* (2013.01);
(Continued)

(58) Field of Classification Search
None
See application file for complete search history.

(56) References Cited

U.S. PATENT DOCUMENTS

| | | | |
|---|---|---|---|
| 5,891,176 | A | 4/1999 | Bornzin |
| 7,672,722 | B1 | 3/2010 | Mengotto |

(Continued)

FOREIGN PATENT DOCUMENTS

WO 2020096982 A1 5/2020

OTHER PUBLICATIONS

International Preliminary Report on Patentability for International Application No. PCT/US2023/063143, dated Sep. 6, 2024, 9 Pages.

(Continued)

*Primary Examiner* — Luther Behringer
(74) *Attorney, Agent, or Firm* — DLA Piper LLP (US)

(57) ABSTRACT

Disclosed are methods, systems, and computer-readable medium for outputting a state machine to determine a next state for a pacemaker, including receiving a plurality of sate machines, each state machine including an algorithm to generate the next state for the pacemaker; receiving a blood pressure value sensed by a blood pressure sensor; receiving a user state; inputting the blood pressure value and the user state at a state machine determination module; determining a first state machine from the plurality of state machines at the state machine determination module, based on the blood pressure value and the user state; and outputting the first state machine to determine new states for the pacemaker.

17 Claims, 7 Drawing Sheets

(52) U.S. Cl.
CPC ....... *A61N 1/3706* (2013.01); *A61N 1/37217* (2013.01); *A61N 1/37252* (2013.01)

(56) References Cited

U.S. PATENT DOCUMENTS

| | | | |
|---|---|---|---|
| 2002/0087146 | A1 | 7/2002 | Schu et al. |
| 2007/0233201 | A1 | 10/2007 | Lovett et al. |
| 2008/0114407 | A1 | 5/2008 | Pastore et al. |
| 2020/0376279 | A1 | 12/2020 | Sharma |

OTHER PUBLICATIONS

Office Action for Israel Patent Application No. 314593, mailed Jan. 29, 2026, 2 pages.
Office Action for European Patent Application No. 23713535.5, mailed Apr. 14, 2026, 9 pages.
International Search Report in International Application No. PCT/US2023/063143, dated Jun. 23, 2023 (3 pages).

SYSTEMS AND METHODS FOR STATE MACHINE SELECTION FOR PACING

CROSS-REFERENCE TO RELATED APPLICATIONS

This is a National Stage application which claims the benefit under 35 U.S.C. § 371 of International Application No. PCT/US2023/063143, filed Feb. 23, 2023, now published as WO 2023/164560 A1, which claims the benefit of priority to U.S. Provisional Application No. 63/268,554, filed on 25 Feb. 2022, and Indian Application No. 202244028218 filed May 17, 2022, each of which is incorporated herein by reference in their entireties.

TECHNICAL FIELD

Various embodiments of the present disclosure relate generally to state machine selection, and, more specifically, to selecting a state machine based on one or more physiological inputs to generate pacing outputs.

BACKGROUND

Pacemaker devices have relied on programming a pacing rate (e.g., atrial pacing rate) using offline methods. For example, pacing rates can be stored and provided to a healthcare provider. The healthcare provider may use the stored pacing rates and/or feedback from a patient to determine updated pacing rates for a corresponding pacemaker. Such updating often requires the patient to visit the healthcare provider and/or a manufacturer to receive the updates. Additionally, such updates do not consider physiological inputs when determining updated pacing rates.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY OF THE DISCLOSURE

According to certain aspects of the disclosure, systems, methods, and computer-readable medium are disclosed for state machine selection. For instance, a method for outputting a state machine to determine a next state for a pacemaker may include: receiving a plurality of state machines, each state machine comprising an algorithm to generate the next state for the pacemaker, where the next state determines a pacemaker pacing output for the pacemaker; receiving a blood pressure value sensed by a blood pressure sensor; receiving a user state; inputting the blood pressure value and the user state at a state machine determination module; determining a first state machine from the plurality of state machines at the state machine determination module, based on the blood pressure value and the user state; and outputting the first state machine to determine new states for the pacemaker.

Furthermore, a system may include a state machine determination module; a pacemaker; a pacing output module; and a processor in communication with the state machine determination module, the pacemaker, and the pacing output module, the processor configured to: receive a first state machine from the state machine determination module based on a blood pressure value; provide the first state machine to the pacing output module; receive a next state from the pacing output module based on the first state machine and the blood pressure value; and provide the next state to the pacemaker.

Furthermore, a method for outputting a state machine to determine a next state for a pacemaker may include: receiving a plurality of sate machines, each state machine comprising an algorithm to generate the next state for the pacemaker, wherein the next state determines a pacemaker pacing output for the pacemaker; receiving a physiological input value sensed by a sensor; inputting the physiological input value at a state machine determination module; determining a first state machine from the plurality of state machines at the state machine determination module, based on the physiological input value; outputting the first state machine to determine new states for the pacemaker; providing the physiological input value to the first state machine; providing a present state to the first state machine; and receive the next state from the first state machine, based on the physiological input value and the present state.

Additional objects and advantages of the disclosed embodiments will be set forth in part in the description that follows, and in part will be apparent from the description, or may be learned by practice of the disclosed embodiments.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION OF EMBODIMENTS

Figure 1A:
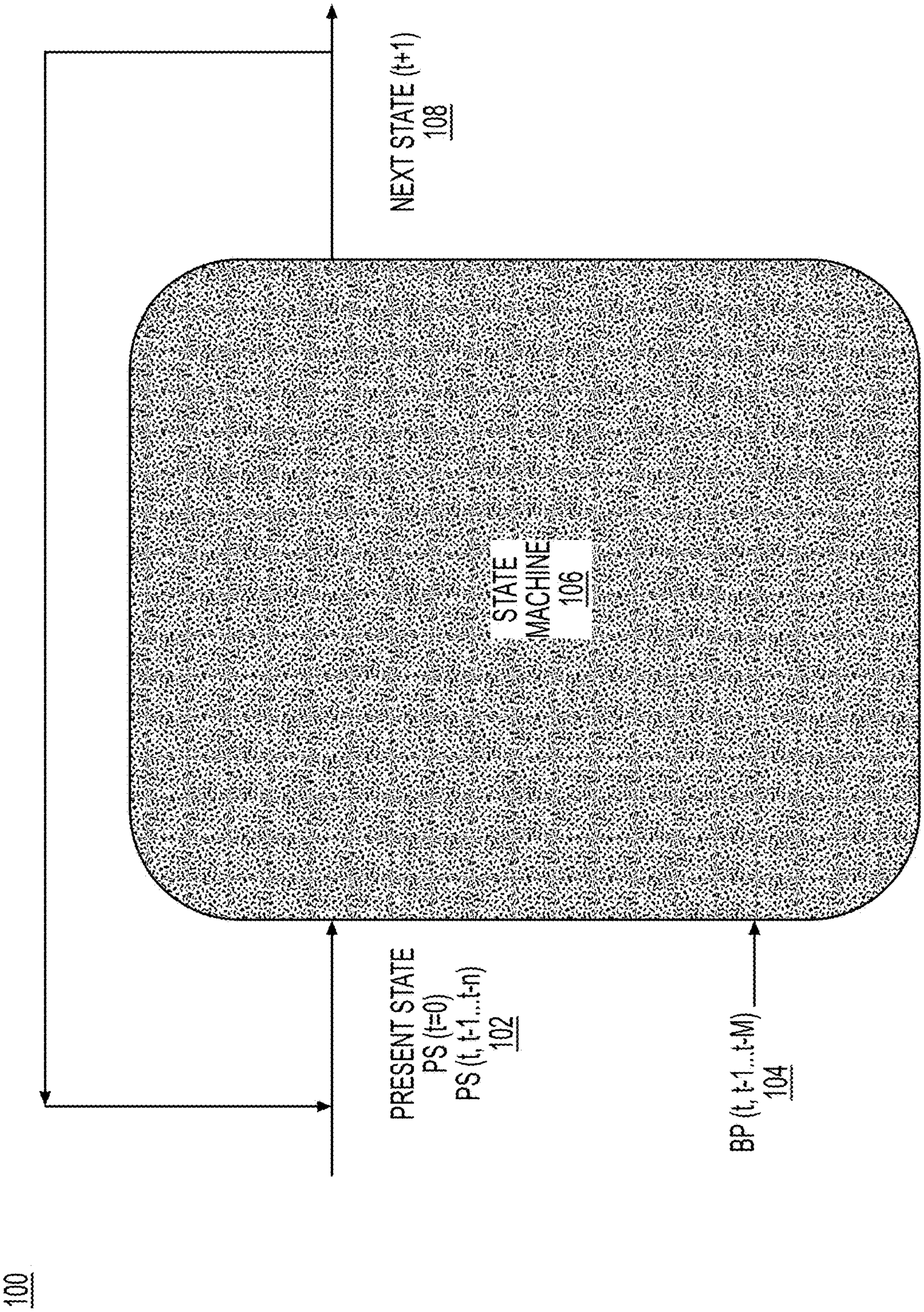
FIG. 1A depicts an exemplary flow diagram for determining states for a pacemaker, according to one or more embodiments.

Various embodiments of the present disclosure relate generally to methods and systems for determining state machines to output states for a pacemaker.

In general, the present disclosure is directed to improving technology used to control a pacing output for a pacemaker. A state machine from a plurality of state machines may be received. Each state machine may include one or more algorithms to determine a next state for a pacemaker. A pacemaker may generate a pacing output based on the next state determined by a given state machine. Each state machine may have a different algorithm for determining next states based on one or more inputs.

A physiological input may be received. The physiological input may be provided by one or more sensors. A physiological input may include, but is not limited to, a blood pressure, a blood oxygen level, glucose level, blood electrolytes level, a heart rate, an accelerometer value, a respiratory rate sensor value (e.g., via diaphragmatic movement), a thoracic impedance, an impedance (e.g., as a correlate of right ventricular function), an environmental parameter, an ambient oxygen concentration (e.g., SPO2), a humidity, portions of cardiac rate such as atrial rate, ventricular rate, atrioventricular conduction, the presence of rhythm irregularities, autonomic nervous system (ANS) function, glucose, skin electrolytes, galvanic skin response, Photoplethysmography (PPG) values, Electroencephalogram (EEG) wave, urination parameters, etc. A physiological input may be supplemented by or may include prescriptions, a gravity value, a barometric pressure, a time of day, meals, emotional states, type of exercises. The one or more sensors may be part of a pacemaker or may be external to the pacemaker. An external sensor may provide the physiological input (e.g., a blood pressure provided via a driver) associated with the external sensor.

A user state may be received. The user state may be an action or activity that a user is undertaking or experiencing. For example, a user state may include, but is not limited to, a user sleeping, exercising, walking, running, or performing another activity. According to an implementation, the user state may be determined based on a heartbeat. The heartbeat may be detected, for example, by a pacemaker or sensor associated with the pacemaker. Alternatively, or in addition, a user state may be provided by a subjective input or an external sensor.

The physiological input and/or the user state may be provided as inputs to a state machine determination module. The state machine determination module may select a state machine from the plurality of state machines, based on the physiological input and/or user state. The state machine determination module may further determine the state machine based on a subjective input (e.g., a user may input a current status or experience via a mobile application). The state machine determination module may further determine the state machine based on historical state outputs (e.g., one or more previous states that the pacemaker used to provide pacing outputs). The historical state outputs may be provided via a user specific data warehouse.

The determined state machine may be provided to a pacemaker processor or external processor such that the pacemaker may receive one or more states based on the determined state machine. The physiological input, the user state, an updated physiological input, and/or an updated user state may be provided as inputs to the processor. The processor may apply the physiological input, the user state, an updated physiological input, and/or an updated user state via the determined state machine. The determined state machine may output a next state based on the inputs, and the pacemaker may generate a pacing output (e.g., electrical impulses) based on the next state.

Accordingly, implementations of the disclosed subject matter may be used to automatically determine an applicable state machine. An applicable state machine may be determined in real time, based on changes in one or more inputs. The applicable state machine may be optimized to output next states, based on physiological inputs and/or user states. The applicable state machine may be optimized to reach a target physiological value (e.g., target blood pressure). Additionally, implementations of the disclosed subject matter may automatically update state machines and, therefore, how next states are determined. The state machines may be automatically updated based on a chronological or event trigger such that a user may not need to interact with a healthcare professional and/or manufacturer to benefit from updated pacing by a pacemaker. Event triggers may allow state machines to automatically update in real time, based on changes in one or more inputs. For example, if an event trigger corresponds to a change (e.g., a threshold change) in a sensed value (e.g., via a physiological sensor), then upon receiving the sensed value, a new state machine may be identified and/or an existing state machine may output a new state, based on the sensed value. Real time, as applied herein, may correspond to events that occur under a threshold time period after a triggering event. For example, the threshold time period may be less than approximately 5 seconds, less than approximately 30 seconds, less than approximately 1 minute, less than approximately 5 minutes, less than approximately 30 minutes, and/or the like.

As also disclosed herein, a data warehouse may store user data (e.g., physiological input data, user state data, state data, pacing output data, etc.). The user data may be stored specific to a given user, such that data associated with a plurality of users is segmented by each user, at the data warehouse. Accordingly, a user's user data may be accessible (e.g., in a raw data format or an analyzed data format) by a processor, pacemaker, or an external device or application.

As also disclosed herein, a device identifier corresponding to a pacemaker associated with a user and/or one or more external devices (e.g., a sensor) may be received. Device identifiers may be provided to the data warehouse. The user data for a given user (e.g., at the data warehouse) may be tagged with the device identifier for the pacemaker and/or one or more external devices associated with a user. Device identifiers may be verified prior to associating user data with a given user or device, thereby mitigating the risk of data contamination.

As discussed herein, a pacemaker may be any suitable therapy or stimulation delivery device. A pacemaker may be any device that outputs electrical signals for one or more operations, including pacing a heartrate. A pacemaker may be a device that is placed (e.g., implanted) at or near the chest of a user to control the user's heartbeat via electrical signals. A pacemaker may be used to prevent the heart from beating too slowly or too fast. A pacemaker may be implanted using a surgical procedure. A pacemaker may generate electrical impulses delivered by electrodes to cause the heart muscle chambers to contract and therefore pump blood. A pacemaker may replace and/or regulate the function of the electrical conduction system of the heart. As discussed herein, a pacemaker may have a pacing output as its final/desired output. Techniques disclosed herein can be applied to treat a pacing as an intermediate outcome that is recalculated automatically until a target physiological output (e.g., target blood pressure) is reached. Techniques disclosed herein may tie physiological inputs (e.g., biomarkers) into a closed loop which can extended to more biomarkers and updated automatically.

As discussed herein a state machine may include one or more algorithms to determine next states for a pacemaker (e.g., for a device that generates electrical impulses). A state machine may determine a next state and output the next state. The next state may be provided to a pacemaker. The pacemaker may generate pacing outputs (e.g., electrical impulses) at a rate, a change in rate, a degree, a frequency, an amplitude, or the like, based on the next state provided by a state machine. For example, a first state machine may increase a pacing rate based on a given physiological input at a faster rate when compared to a second state machine, based on the same inputs.

As discussed herein, a next state may be output by a state machine. The next state may be an update from a current state based on which a pacemaker provides pacing outputs. The next state may output different pacing outputs based on the same inputs (e.g., physiological inputs, user states, heartbeat, etc.) based on different state machines.

As discussed herein, a user state may include, but is not limited to, a user sleeping, exercising, walking, running, or performing another activity. According to an implementation, the user state may be determined based on a heartbeat. The heartbeat may be detected, for example, by a pacemaker or sensor associated with the pacemaker.

As discussed herein, a memory may include a device or system that is used to store information for immediate use in a computer or related computer hardware and digital electronic devices. Memory may operate at a high speed compared to storage, as discussed herein. Storage may provide slower access to data in comparison to memory. Contents of memory can be transferred to storage (e.g., via virtual memory). Memory may be implemented as semiconductor memory, where data is stored within memory cells built from MOS transistors on an integrated circuit. Semiconductor memory may include volatile and/or non-volatile memory. Examples of non-volatile memory include flash memory and read-only memory (ROM), programmable read-only memory (PROM), erasable programmable read-only memory (EPROM), electrically erasable programmable read-only memory (EEPROM) memory, and the like. Examples of volatile memory include primary memory such as dynamic random-access memory (DRAM) and fast CPU cache memory such as static random-access memory (SRAM).

Traditional pacemaker devices have relied on programming the pacing rate using offline methods. Real time physiological input are not used in the programming of pacemakers unless gathered by the pacemaker system internally. Traditional pacemakers have relied solely on parameters collected by the built-in hardware for their routine operation. Additionally, traditional systems do not provide any modality for user input or intervention.

Rate modulation may be performed by the addition of an accelerometer to the pacemaker that senses bodily motion and provides the occurrence and magnitude for pacing. However, traditional modulation is programmed empirically and cannot be adjusted in real-time. For example, with traditional devices, a patient with a pacemaker and Sinus Node Dysfunction who reports fatigue with exercise has his/her rate modulation pacemaker feature empirically programmed by a healthcare provider or pacemaker technician, based on the patient's assessment of how much rate modulation (e.g., a scale of 1-10 in intensity, and 1-10 in rate of rise) the patient may benefit from. Often such assessment is followed by a walk in a hallway to confirm that the degree of heart rate acceleration does not cause palpitations or chest pain by being excessive. A programming change is made and is not adjusted until a subsequent clinic visit. However, a patient may, for example, exercise to varying degrees not simulated by the hallway walk and may need real time rate modulation (e.g., higher settings) or less rate modulation when greater acceleration causes palpitations or chest pain. Traditionally, such discrepancies are resolved by another healthcare or technician visit.

Myocardial electrical activities other than ECG signals have been used in traditional pacemakers. However, such activity is limited to cardiac signals and does not incorporate or address physiological properties.

Some traditional pacemakers attempt to measure transthoracic impedance as an indirect measure of lung water. However, in such systems the vector for measurement is limited to the distance between the metal pacemaker and the pacemaker lead tips. Additionally, other pathophysiologic states, such as pneumonia can increase lung water but not be associated with heart failure. Such pacemakers cannot be programmed or accessed in real time.

Techniques disclosed herein disclose a novel finite state machine (state machine) for the regulation of physiological properties (e.g., blood pressure) in patients with implanted pacemakers and, for example, Drug Resistant Hypertension/HFpEF. The finite state machine may be configured to receive physiological inputs such as systolic and diastolic blood pressures and adjust the pacing output in real time, resulting in reduced systolic/diastolic blood pressure.

Techniques disclosed herein provide a new architecture for pacemaker control with a modified state machine architecture that can accept and process a physiological input, such as blood pressure, in addition to a present state and/or it's time series. Multiple transform functions via different state machines may be superimposed on the factory defaults of a pacemaker, without having to invoke a manufacturer or health care professional review process. Artificial intelligence/machine learning algorithms or patient specific or context specific transformation may be superimposed. Transform function(s) via state machines may be varied as an output of a finite state machine, in addition the next state of the pacemaker being an output. As disclosed, a state machine may consider a historic time series of physiological data as input to the transform functions.

According to implementations disclosed herein, one or more physiological inputs may be used to determine pacing outputs (e.g., pacing rates). Updated pacing outputs (e.g., based on a next state of pacemaker) may be computed external to a pacemaker without the intervention of a physician. The updated pacing outputs/next states may be computed, for example, at a cloud device, server, processor or the like. Pacing outputs may be computed in real time and communicated to pacemaker and/or its controller. A heart rate may be provided by a pacemaker (e.g., sensed from intrinsic cardiac activity) collected retrograde by pacemaker leads within, for example, a time frame of two heart beats. A pacing output may correspond to a heartbeat when a pacemaker is the source of the heartbeat. If a heart rate intermittently falls below a lower rate limit of a pacemaker, it is possible for the pacemaker to support a heartbeat (e.g., for a single heart beat) as the pacemaker may predict the impending heart rate and send stimulus to pace whenever a next heart beat may be below the lower limit. State machines may include algorithms to compute pacing outputs that can be varied without a telemetry transaction and without a visit to a clinical facility. State machines with algorithms to compute pacing outputs can be dynamically varied based on patient context or condition, and can be personalized to a patient in an automated manner. Additionally, device identifiers may be used to authenticate communications using in, eliminating the need to login (e.g., using a username/password).

Techniques disclosed herein may be implemented using a user device such as a smartphone or tablet, or a program residing on a computational host on which pacemaker functions can be virtualized using a software and or graphical user interface (GUI). One or more processors disclosed herein may be controlled using a software device/application that receives inputs (e.g., a physiological input, a current status, subjective inputs, sensor inputs, etc.) from an implanted device or external device. Techniques disclosed herein may be software agnostic such that one or more drivers or application programing interfaces (APIs) may be used to communicate with any applicable software.

FIG. 1A depicts an exemplary flow diagram 100 for determining a next state 108 for a pacemaker. As discussed herein, a pacemaker may be any suitable therapy or stimulation delivery device. A present state 102 may be provided based on a current pacing output of a pacemaker or may be provided from a previous output of state machine 106. Present state 102 may include a pacing output (e.g., pacing rate), as well as one or more current or previous parameters (e.g., pacing rate, change in rate, degree, frequency, amplitude, etc.) for pacing. According to an implementation, present state 102 may include one or more historical states for a given pacemaker. The historical states may be stored in a volatile or non-volatile memory, may be retrieved from a data warehouse, and/or may be stored remotely (e.g., in a cloud storage, database, memory, etc.).

Physiological blood pressure value 104 may be detected by a blood pressure sensor that is internal or external to a pacemaker. For example, physiological blood pressure value 104 may be detected by a wearable device configured to sense a blood pressure value. Physiological blood pressure value 104 may be a systolic and/or diastolic blood pressure value. It will be understood that although blood pressure is generally disclosed herein as a physiological parameter, one or more other physiological parameters may be substituted to implement the techniques disclose herein.

Present state 102 may be provided automatically or based on a chronological or event based trigger. An example of a chronological trigger may be a time of day. An example of an event based trigger may be a change in heartrate, a change in user state, a user input, a physiological change, or the like. An event based trigger may be determined based on a sensor based input from a sensor. For example, an external or internal blood pressure monitor may detect a change in blood pressure by at least a threshold amount. The change of the blood pressure by a threshold amount may be the event based trigger. Similarly, physiological blood pressure value 104 may be provided automatically or based on a chronological or event based trigger.

Accordingly, a next state 108 may be generated based on a push and/or pull mechanism. A chronological trigger (e.g., a given time) may trigger a pull for inputs (e.g., present state 102 and a physiological blood pressure value 104). The chronological triggers may be parametrized and/or preprogrammed or may be dynamically determined. For example, a machine learning algorithm may receive user data (e.g., from a data warehouse) as inputs. The machine learning algorithm may determine that, based on a given user's user data, chronological triggers at 7 AM and 8 PM should be implemented. The machine learning algorithm may update the chronological triggers over time based on updated user data. For example, based on a change in user data as a result of a change in the user's sleep patterns, the machine learning algorithm may update the chronological triggers to 8 AM and 9 PM.

Additionally, next state 108 may be generated based on a push. An event based trigger (e.g., based on sensor inputs, user inputs, etc.) may push a request for updated input data (e.g., present state 102 and a physiological blood pressure value 104).

As shown in FIG. 1A, a state machine 106 may provide a next state 108 output based on a present state 102 and a physiological blood pressure value 104. Next state 108 may be output by state machine 106 such that an algorithm associated with state machine 106 calculates one or more next state 108 parameters based on the present state 102 and a physiological blood pressure value 104. As a simplified example, state machine 106 may generate a next state 108 parameter (pacing rate) based on the following:

```
Parameter HIGHVAL, LOWVAL;
Input BP, PS;
If (BP>HIGHVAL) next_state_pacing_rate=+10;
Else IF (BP<LOWVAL) next_state_pacing_rate=−10;
```

According to this implementation, a pacemaker may receive next state 108 and may generate pacing outputs based on the parameters (e.g., pacing rate, change in rate, degree, frequency, amplitude, etc.) provided via next state 108.

According to implementations of the disclosed subject matter, state machine 106 may be external to a pacemaker device to which state machine 106 provides next state 108. For example, state machine 106 may be located at a cloud server, database, device, etc. State machine 106 may receive inputs (e.g., obtaining information about the keyword) via a network connection (e.g., internet connection). State machine 106 may generate next state 108 and may transmit next state 108 via the same or a different network connection. According to another example, state machine 106 may be operated using a user device (e.g., a mobile phone, tablet, wearable device, computer, etc.). State machine 106 may be stored on the user device or may be stored using a cloud component and may be accessed using the user device. The user device may receive inputs (e.g., obtaining information about the keyword) via a network connection (e.g., internet connection). The user device may provide the inputs to state machine 106 located on the user device or in a cloud component.

According to an implementation, a GUI on a user device may be used to control and/or view operation of a pacemaker and/or one or more state machines. For example, state machine outputs may be displayed on a user device via the GUI. As another example, a user may provide subjective inputs (e.g., of a user state, of a user experience, etc.) via a GUI on a user device. The subjective input may be provided to a state machine 106 and/or to identify a state machine from a plurality of state machines, as further disclosed herein. The subject input may be received at a state machine determination module (e.g., a processor) that identifies a state machine from a plurality of state machines based on the subjective input.

Figure 1B:
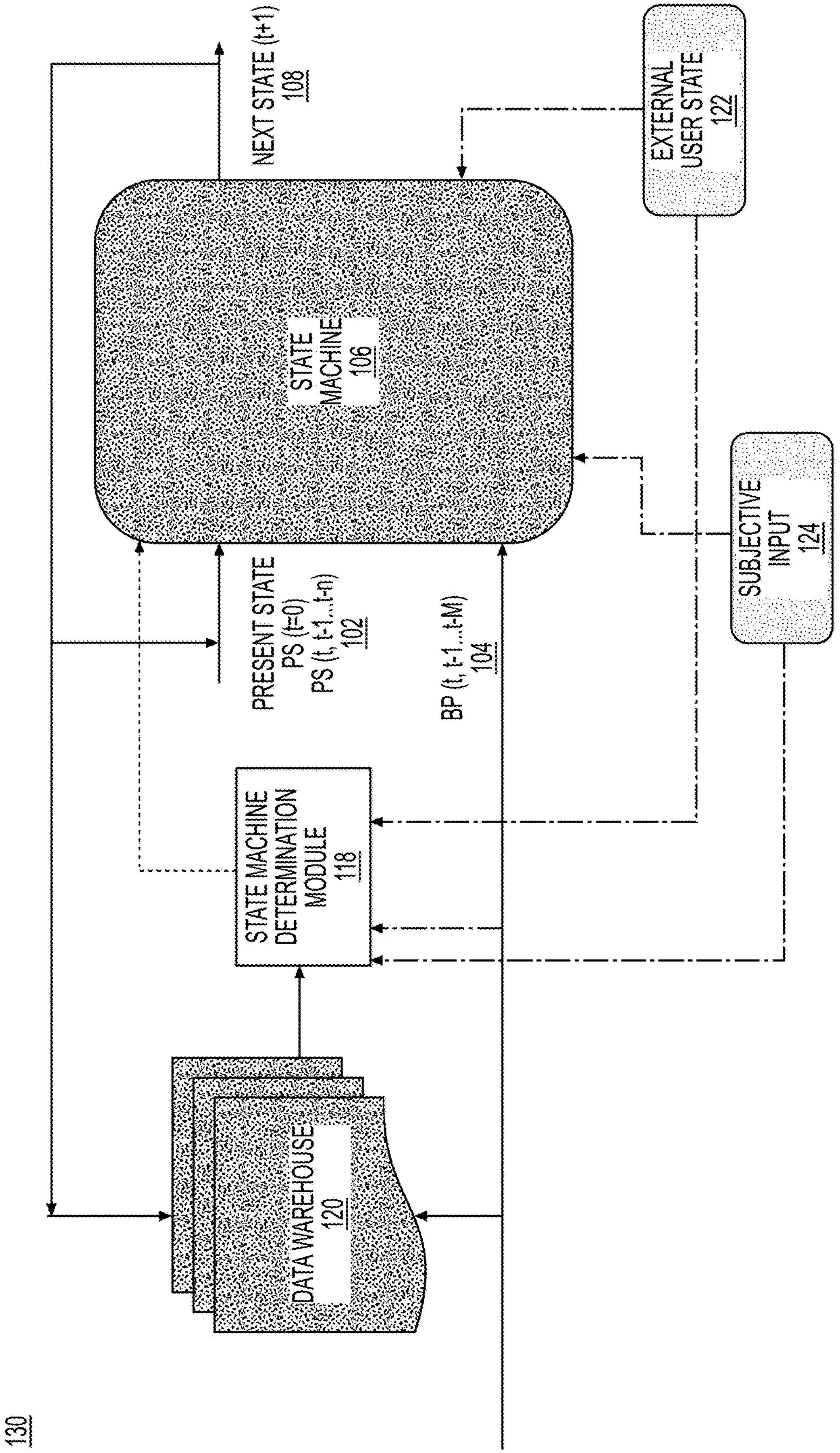
FIG. 1B depicts an exemplary flow diagram for determining state machines, according to one or more embodiments.

FIG. 1B depicts an exemplary flow diagram 130 for determining state machines. The present state 102, physiological blood pressure value 104, state machine 106, and next state 108 shown in FIG. 1A are reproduced in FIG. 1B.

A state machine determination module 118 may be configured to output state machine 106 from a plurality of state machines. As discussed herein, a state machine may be implemented using a software or firmware application. A state machine may include one or more algorithms to output next states. For example, a state machine may be stored or accessed via a smart phone (e.g., an application that accesses state machines from a memory, storage, or cloud component) that receives inputs and outputs a next state to, for example, a pacemaker (e.g., a device configured to output electrical signals). State machine determination module 118 may output state machine 106 based on one or more inputs. The one or more inputs may include, but are not limited to a physiological input (e.g., physiological blood pressure value 104), user state 122, subjective input 124, a current state (e.g., next state 108 output to a pacemaker), user data (e.g., from data warehouse 120). Data warehouse 120 may store user data in a segmented manner, as disclosed herein.

State machine determination module 118 may output state machine 106 from a plurality of state machine to effect a physiological value (e.g., blood pressure). The effect may be to reach a target physiological value such that next states output by the output state machine 106 may cause a pacemaker to generate a pacing output to reach the target physiological value.

State machine determination module 118 may determine an updated state machine based on one or more factors, as disclosed herein. For example, state machine determination module 118 may be triggered to determine an update state machine based on user input (e.g., subjective input 124), based on a healthcare provider input, based on a change in physiological input (e.g., physiological blood pressure value 104), a chronic trigger, an event trigger, a change in a user state (e.g., as determined by a sensor or input, such as external user state 122, a preset (e.g., a physical action or exertion, a social event, etc.), a historical pattern based trigger, an algorithm, or the like. The state machine determination module 118 may be configured to continuously determine if an updated state machine is determined. The continuous operation may monitor (e.g., based on signal inputs and/or lack of signal inputs) activity, target physiological values, current physiological values, or the like, to determine if an updated state machine should be determined. Such continuous operation may be conducted without a request (e.g., by a health care provider) to update the state machine, though such a request may also trigger determining a new state machine.

According to implementations of the disclosed subject matter, as further described in WO2020096982A1, which is incorporated herein by reference in its entirety, regulation of pacemaker function by blood pressure may be used to treat drug resistant hypertension (DRH) and/or DRH with diastolic congestive heart failure (DCHF). State machine learning module 118 may determine optimal pacemaker function by outputting an applicable state machine that outputs next states to better treat DRH and DCHF.

For example, a current blood pressure (e.g., physiological blood pressure value 104) and a target blood pressure may be identified for a given user. The target blood pressure value may be predetermined or dynamically determined (e.g., based on the current blood pressure value, by a machine learning model, based on a user state, etc.). Accordingly, state machine determination module 118 may receive physiological blood pressure value 104, a user state (e.g., via a heartbeat from the pacemaker or external device, via external user state 122, etc.), subjective input 124, user data (e.g., from data warehouse 120 that may include historical data for the user), or the like. Based on these inputs, state machine determination module 118 and/or a machine learning model associated with state machine determination module 118 may output state machine 106. State machine 106 may be selected from a plurality of state machines based on the inputs such that, based on the inputs, state machine 106 may be best configured to output next state(s) 108 to reach the target blood pressure.

A user state may be determined based on sensor data (e.g., a heartbeat, a sensed signal by external user state 122, etc.) or may be input by a user (e.g., via subjective input 124). The user state may be provided by, for example, a pacemaker in communication with state machine determination module 118 and/or by an external user state 122. The user state may be used as an input to output state machine 106 (e.g., by state machine determination module 118) and/or next state (e.g., by state machine 106).

Figure 2:
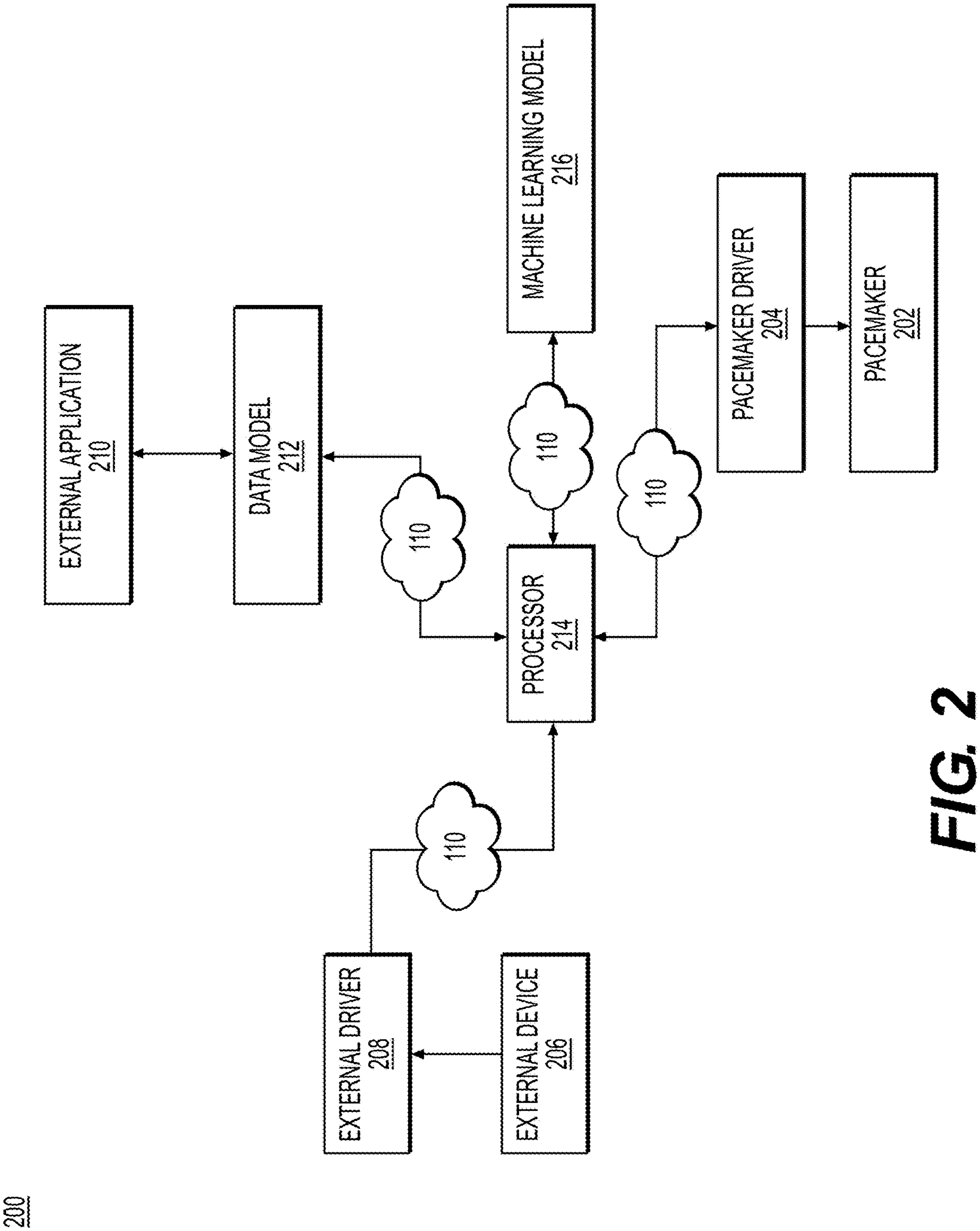
FIG. 2 depicts a system diagram for a pacing system, according to one or more embodiments.

FIG. 2 depicts a system diagram 200 for a pacing system. As shown in FIG. 2, a processor 214 may receive inputs from one or more of an external device 206, external driver 208, external application 210, data model 212 (e.g. where data model 212 is an interface of a data warehouse), machine learning model 216, pacemaker driver 204, pacemaker 202, or the like.

Processor 214 may be at a user device, a pacemaker, at a standalone device, or at a cloud component. According to an implementation, processor 214 may communicate with one or more components over network 110.

External device 206 may be subjective input 124, external user state 122, a sensor (e.g., physiological value sensor), a wearable device, a user device (e.g., a mobile phone, a tablet, a computer, etc.), or the like. It will be understood that external device 206 may be a combination of devices.

External driver 208 may receive data from external device 206 in one or more formats. External driver 208 may be configured to convert data from eternal device 206 into a format that is accepted by processor 214. For example, external driver 208 may be a software component that functions as an API. Accordingly, external driver 208 may receive data from external device 206 and apply one or more functions to the data. The application of the one or more functions may covert the received data into a new format that is accepted and/or used by processor 214. According to an implementation, external driver 208 may communicate with processor 214 to determine the format required by processor 214.

External application 210 may be a third party application or a software application. Processor 214 and/or data model 212 may be configured to communicate with a plurality of external applications 210 such that the system is application agnostic. One or more APIs or applicable communication mediums may be used to communicate with an applicable external application 210. External application 210 may receive data from a data warehouse via data model 212 and/or may provide data to a data warehouse via data model 212. According to an implementation, a subscription tier for external application 210 may be determined (e.g., by data model 212). Based on the determined subscription tier, an amount, type, and/or format of data may be received from or provided to external application 210. For example, data model 212 or underlying data warehouse may be configured to store raw user data. Additionally, data model 212 or underlying data warehouse may be configured to perform analysis on the raw data. Accordingly, analyzed data based on the raw data may be stored at the data warehouse and may be accessed via data model 212. Based on the determined subscription tier, the data (e.g., raw data) and/or analyzed data may be provided to external application 210. For example, a higher tier subscription may allow for access to the analyzed data whereas a lower tier subscription may allow access to the raw data without allowing access to the analyzed data.

Machine learning model 216 may be trained to output one or more of a state machine, a next state, or the like. Machine learning model 216 may receive inputs (e.g., from processor 214) and may process the inputs through the model. Machine learning model 216 may also receive feedback from processor 214 such that subsequent outputs from machine learning model 216 may be adjusted based on the feedback.

According to an example, a state machine may be output by the machine learning model. The state machine may determine one or more next sates that are provided to a pacemaker, to achieve a target physiological value based on pacing outputs by the pacemaker. Processor 214 may generate feedback (e.g., if the target physiological value is reached, if it is reached in a given time period, if it is not reached, etc.). The feedback may be provided to machine learning model 216 such that machine learning model 216 adjusts one or more weights or layers to improve subsequent outputs. Accordingly, subsequent outputs provided by machine learning model 216, based on the same input data as one or more previous iterations, may be different (e.g., optimized to reach the target physiological output).

Processor 214 may communicate with pacemaker 202 (e.g., over network 110) via pacemaker driver 204. Pacemaker driver 204 may be configured to convert data from pacemaker 202 into a format that is accepted by processor 214. For example, pacemaker driver 204 may be a software component that functions as an API. Accordingly, pacemaker driver 204 may receive data from pacemaker 202 and apply one or more functions to the data. The application of the one or more functions may covert the received data into a new format that is accepted and/or used by processor 214. According to an implementation, pacemaker driver 204 may communicate with processor 214 to determine the format required by processor 214. Accordingly, it will be understood that the implementations disclosed herein may be pacemaker agnostic such that one or more different types or brands of pacemakers may be used to implement the techniques disclosed herein. Indeed, the methods and apparatus described herein may be implemented in connection with any suitable therapy or stimulation delivery device.

Accordingly, techniques provided herein disclose a closed loop system. In the closed loop system, pacing outputs may be adjusted via one or more state machines, to reach a target physiological value. For example, pacing outputs may be adjusted to reach a target blood pressure. The pacing outputs may be adjusted by receiving updated next states from a state machine. For example, a state machine may receive inputs (e.g., physiological inputs, user states, historical states, current state, subjective input, etc.) and may output a next state based on the inputs. The next state may be used by a pacemaker to generate pacing outputs to reach the target physiological value. Alternatively, or in addition, pacing outputs may be adjusted by receiving an updated state machine (e.g., from a state machine determination module). For example, a state machine determination module may output an updated state machine based on one or more inputs (e.g., physiological inputs, user states, historical states, current state, subjective input, etc.). The updated state machine may be, for example, better optimized to reach the target physiological value based on the input data, then a current/previous state machine. Accordingly, a pacemaker may receive a next state and generate pacing outputs based on the updated state machine. Such a closed loop system allows for adjustments to both next states and/or state machines to reach target physiological values without needing intervention (e.g., by a healthcare provider, a technician, etc.).

Figure 3:
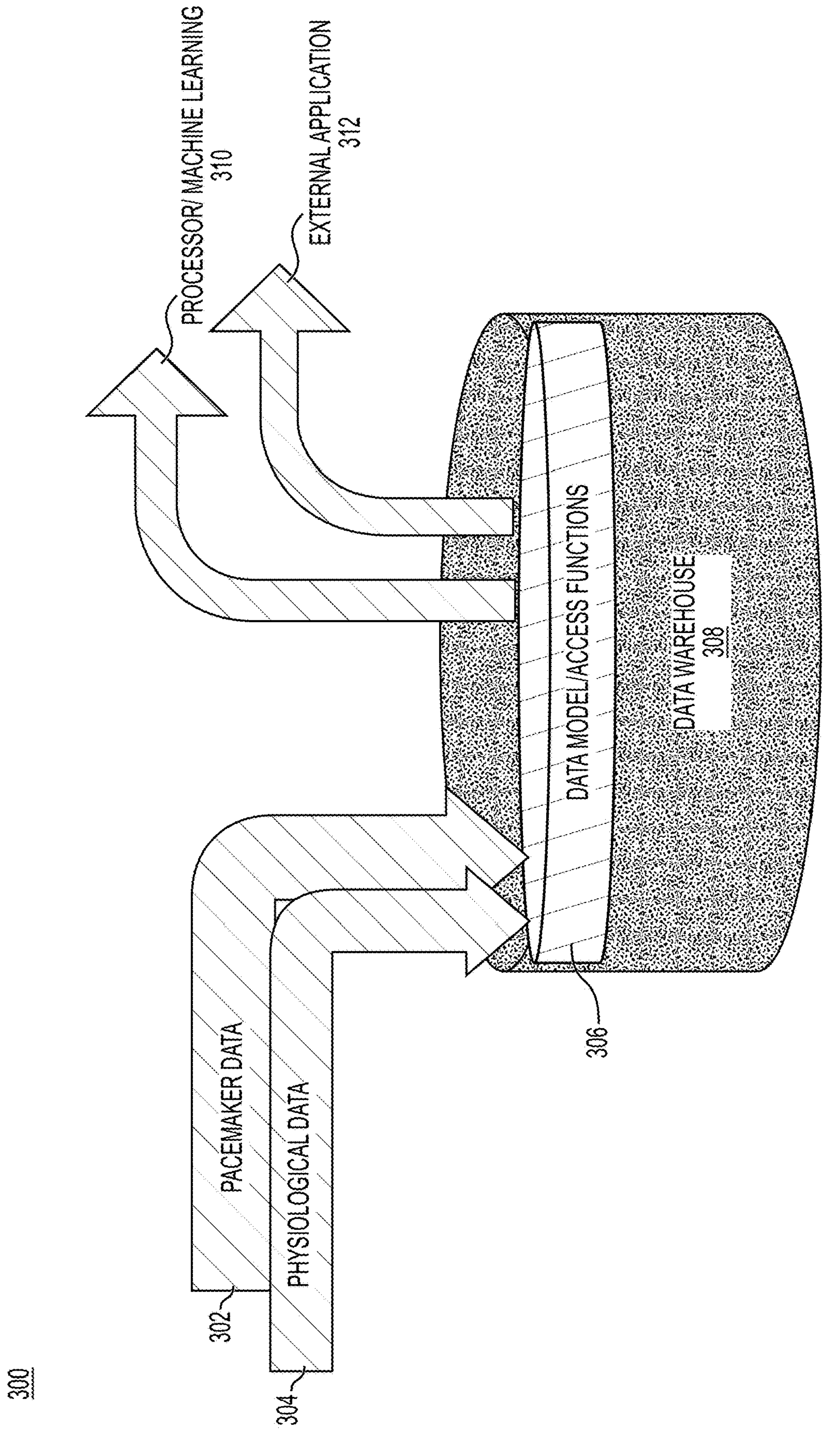
FIG. 3 depicts a flow diagram for using a data warehouse, according to one or more embodiments.

FIG. 3 depicts a flow diagram for using a data warehouse. Pacemaker data 302 and physiological data 304 (e.g., blood pressure values) may be provided as inputs to a data model 306 with access functions and may be stored at data warehouse 308. As shown in FIG. 1B, additional inputs (e.g., user state, subjective input 124, external user state 122, next state 108, etc.) may also be provided as inputs to a data model 306 with access functions and may be stored at data warehouse 308. As disclosed herein, data warehouse 308 may store user data (e.g., the inputs) in a segmented manner such that a given user's user data may be packaged separately from another user's user data. Accordingly, a first user's data may be packaged and/or stored separate from a second user's data. By segmenting user data, a given user's data can be packaged for use by a processor/machine learning model 310, an external application 312, or the like.

Figure 4:
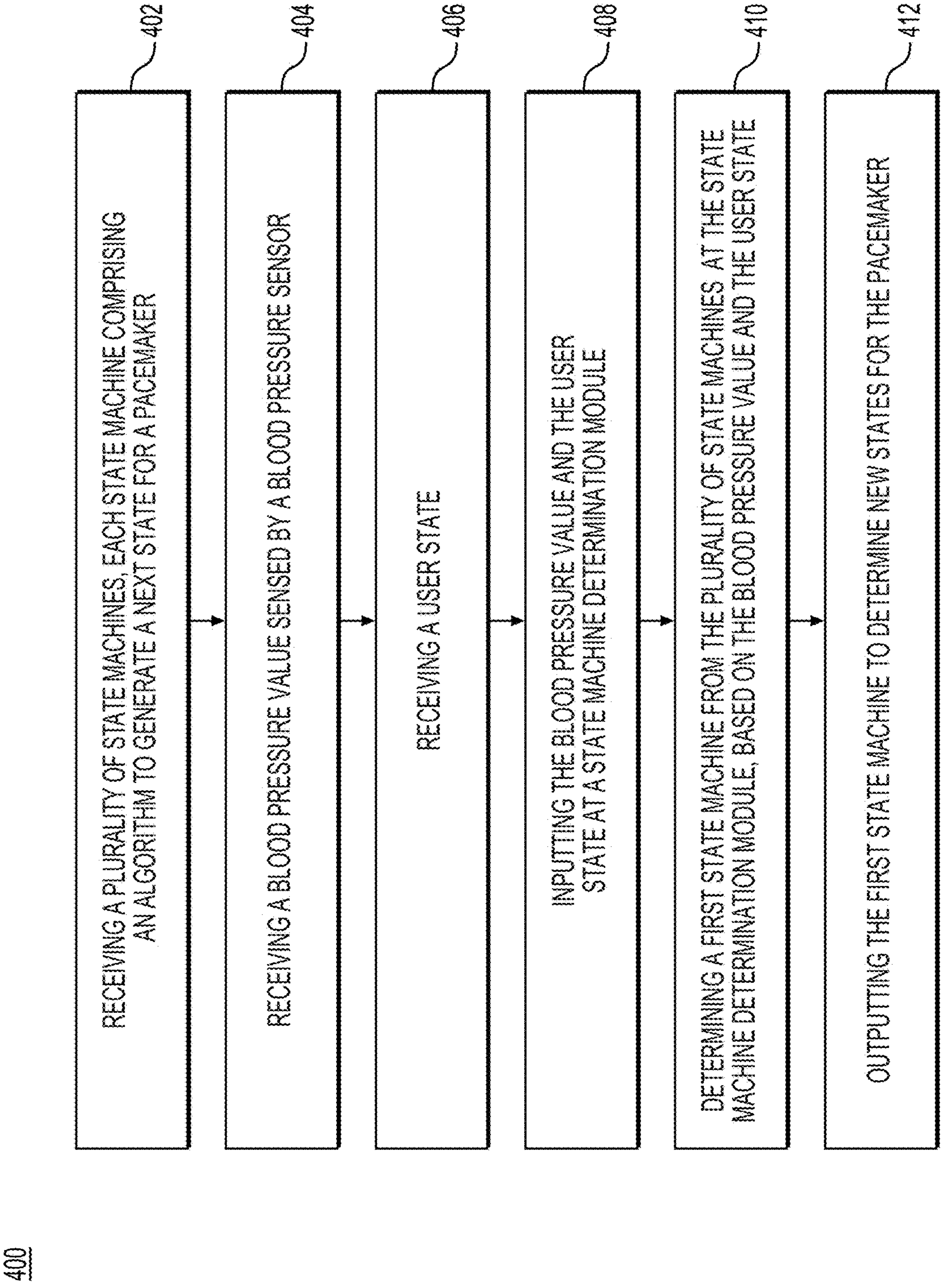
FIG. 4 depicts a flowchart for determining state machines, according to one or more embodiments.

FIG. 4 depicts a flowchart 400 for determining state machines. At 402, a plurality of state machines may be received. The state machines may be received at a cloud component, a pacemaker, and/or a component with a processor. Each state machine may include one or more algorithms to generate next states for a pacemaker. At 404, a blood pressure value may be sensed by a blood pressure sensor. The blood pressure sensor may be associated with a pacemaker or may be an independent component (e.g., part of a wearable device). At 406, a user state may be received. The user state may be based on, for example, a heartbeat (e.g., detected by a pacemaker or other component). The user state may be received based on a subjective input. At 408, the blood pressure value and the user state may be input at a state machine determination module. At 410, the state machine determination module may determine a first state machine from the plurality of state machines, based on the blood pressure value and user state. At 412, the first state machine may be output to determine new states for the pacemaker. The pacemaker may receive one or more new states from the first state machine. The pacemaker may generate pacing outputs based on the one or more new states. One or more steps of flowchart 400 may be repeated until a target blood pressure is reached.

According to implementations of the disclosed subject matter, user data (e.g., user data stored in a data warehouse) may be configured and/or organized to identify changes a state (e.g., next state) output by a state machine in a continuous, autonomous, and/or field programmable manner. Implementations disclosed herein provide a software defined system to update state machines, next states, etc. Such software based applications provide for the accumulation of data parameters into a user/patient specific data warehouse resident within each applicable instance. The data warehouse may aggregate historic/longitudinal values of parameters such as physiological data (e.g., blood pressure values), pacing rate etc. Accordingly, the data warehouse may be configured to provide access to such user data to one or more programs/algorithms. As disclosed herein, such access maybe in the form of raw data (e.g., physiological data, time stamps, etc.) and/or as functions that are pre-processed outputs on the data gathered. For example, a data warehouse may output an average blood pressure on a given data. As another example, a data warehouse may output a derivative of a pacing rate for a given time range.

The formation of such functions may infinite and may not be pre-defined. For example, as disclosed herein, a machine learning model may generate such functions based on input data, on an ongoing continuous basis. A corresponding data model may be provided as an object that can be accessed and/or manipulated (e.g., by a processor, by an external or third party application, by a pacemaker, etc.).

A data warehouse may be a repository whereas the data model may be an access method for both raw and/or processed user data/functions. Therefore, the data model may provide the basis for external or third party functions/applications that can be applied using the systems disclosed herein.

Additionally, a processor, software, or other component may receive data from a data warehouse to inform state machine selection (e.g., via state machine determination module 118). However, it will be understood that one or more other inputs may also inform the state machine selection (e.g., as shown in FIG. 1B). A data warehouse may be segmented such that a segment of the data warehouse is intrinsically tied to a given user, a given model of pacemaker, and/or given sensors (e.g., sensors used to measure blood pressure).

As disclosed herein, a device identifier may be associated with a device (e.g., a component shown in FIG. 1A, 1B, 2, or 3). For example, when a pacemaker is implanted into a user, a unique device identifier may be matched to a specific patient. The particular device identifier and/or instance of a device identifier of a pacemaker may be used to tag user data generated by the pacemaker. The device identifier may be used to meet traceability requirements, communicate with other devices, etc.

Accordingly, a system of components with unique device identifiers (e.g., pacemaker, sensor, user device, etc.) may be associate with a patient. A data warehouse for a given user may be tagged with the component device identifiers, defining a closed system of components for a given user. User data that does not match one or more device identifiers with a given user may be rejected to maintain user data authenticity. One or more software, devices, or interfaces may be used to add/modify/remove device identifiers from a system of components associated with a user. For example, if a user starts using a new pacemaker, the new pacemaker's device identifier may be added to the user's system of components.

According to an implementation, device identifiers may be used to provide seamless operation of techniques disclosed herein. A device identifier may trigger calibration or updating. For example, if a particular model of a component (e.g., a blood pressure sensor) used by a patient is replaced, the recognition of data from a different source may allow for a recalibration step of the new device's readings. A device identifier may be used to facilitate the re-calibration (e.g., based on data associated with a previous device identifier). Accordingly, state machine determination and/or next state determination may remain seamless across multiple devices.

Device identifiers associated with user data may allow for personalizing of the user data. A set of user data tied to one or more device identifiers provides repository that is unique to the patient. Accordingly, a data model built upon such a warehouse (e.g., user specific data) is unique to a given patient. Algorithms that rely on access functions to the data warehouse/data model are likely to return unique results that are patient specific.

According to implementations of the disclosed subject matter, a user may affect his or her pacemaker operation (e.g., via subjective input 124 of FIG. 1B). Allowing a user to affect his or her own pacemaker programming as part of an automatic closed loop system of control of a pacemaker allows for using any non-pacing parameter to control the pacemaker.

For example, standard rate modulation may be used. A user may have his/her rate modulation sensor initially calibrated by a supervising physician in person or remotely. The user may later feel his/her heart pounding. The disclosed implementations allow the user to provide subjective input 124, remotely (e.g., using a user device), to provide an input. The input may be received by state machine 106 and may reduce the pacing output, disable pacing, or return to prior settings until supervising physician can become involved, based on the input.

Subjective input 124 may be used for selection of a pacing method. For example, subjective input 124 may be used to select whether the pacing (e.g., via next state 108) is primarily or wholly based on one of a plurality of targets (e.g., to reach a target blood pressure, to reach a target heart rate, to reach a target blood oxygen level, etc.).

A machine learning or artificial intelligence program may be used to adjust a next state if, for example, a user has an adverse response from a current state. Such an adjustment may be made automatically based on the state machine receiving one or more inputs corresponding to the adverse response.

According to an implementation, subjective input 124, external user state 122, and/or one or more other inputs may be used to provide physiologic safeguards, connectivity safeguards. For example, a state machine may be selected to implement a given safeguard, based on or more inputs to state modulation determination module 118. As another example, a next state may be selected to implement a given safeguard, based on one or more inputs to state machine 106.

According to an implementation, a safeguard may be implemented automatically without supervision. Safeguards may include a kill switch function or may be implemented based on subjective input 124, as disclosed herein. For example, if a user or sensor provides an input that a reprogramming event (e.g., a next state based pacing output) has resulted in adverse symptoms, the user or sensor output relied upon to abort that reprogramming and the system may automatically default to a safe mode or be suspended via the kill switch. The default to a safe mode may correspond a prior setting or to a setting when the user or sensor indicated that the user was in an acceptable state (e.g., the user felt comfortable).

According to an implementation, a triggered safeguard may result in a gradual return to a different (e.g., prior) setting. For example, in the event of atrial fibrillation (AF), if a sensor detects AF (e.g., when a heart rate is very fast and/or erratic), a next state may be output that defaults to a ventricular back pacing rate by dropping the rate slowly over several minutes.

Subjective input 124 may be provided via a score, selection of a scale, selection of one of a plurality of options (e.g., buttons), or the like. Receipt of subjective input 124 may alert the system or component (e.g., state machine determination module 118, state machine 106, etc.) that the user is feeling well and can proceed with the next state. Such input may also allow the user to provide an input that a new state and/or corresponding pacing output caused adverse symptoms such as shortness of breath and/or palpitations. Such subjective inputs may trigger a safeguard to protect users from adverse remote reprogramming events with adverse outcomes.

According to an implementation, if wireless communication is lost, a safeguard may be implemented (e.g., kill switch, reversion to a prior state, etc.). The safeguard may be implemented via protected communication to a server. An alert may be provided to a safeguard monitoring entity.

According to an implementation, if a physiological sensor (e.g., a blood pressure cuff) fails to supply a physiologic value (e.g., blood pressure) defined within an applicable range, a repeat reading may be requested. If the repeat reading is outside the applicable range, a safeguard may be triggered and/or an alert may be provided to a safeguard monitoring entity.

According to an implementation, a wearable and/or home module may include an internal clock that prevents new states from being implemented outside of prescribed times of day. For example, this restriction may be used with a two-time-a-day reprogramming to treat resting hypertension, but may not be applied, for example, when a user is determined to be exercising.

According to implementations of the disclosed subject matter blood pressure measurement, such as a sphygmomanometer or optical measurements (e.g., photoplethymography) may be provided (e.g., wirelessly). State machines may be stored (e.g., in cloud, remote, or user devices) and may be provided (e.g., wirelessly). A dual chamber pacemaker may generate pacing outputs based on next states, as disclosed herein. For example, a system to implement the disclosed subject matter may include a sphygmomanometer, smartwatch, tablet, and/or a pacemaker. A user with drug resistant hypertension may use the sphygmomanometer (e.g., twice a day) to measure blood pressure values and transmit the blood pressure values to a tablet. A state machine determination module and/or state machine may be accessed via the tablet (e.g., via a network connection, or via a memory or storage associated with the tablet). The blood pressure values may be provided to the state machine determination module and/or state machine. The state machine determination module and/or state machine may be used to output an optimal right atrial pacing rate, via a next state, to treat the blood pressure to reach a target blood pressure.

According to an example implementation, a photoplethysmographic (PPG) blood pressure measurement may be provided by a PPG sensor (e.g., a sensor in a smart watch). The PPG sensor may be calibrated to medical grade accuracy using the blood pressure from a sphygmomanometer. The resulting calibrated PPG blood pressure may then be measured every two minutes for 24 hours. Based on the calibrated PPG blood pressure, a next state for right atrial pacing and any applicable updates may be provided every two minutes. Such inputs may be provided both at rest and during activity performance (e.g., during exercising).

As discussed herein, subjective inputs may be received from a user. For example, prior to the initiation of any programming changes, a user may provide responses to a question are (e.g., via a GUI). An example question may be "do you feel well enough to proceed?" If the answer is "NO", the cycle may aborted and a message may be sent to a processor or cloud component indicating the same. Similarly, if a programming cycle has been completed and the results of pacing based on the programming (e.g., based on pacing outputs determined based on the programming) is the patient feels less well (e.g., has a pounding heartbeat), the cycle and corresponding programing may be aborted. A message may be sent to a processor or cloud component indicating the same.

The programming, associated data, and applicable next states and/or state machines may be provided to a data warehouse (e.g., a cloud component). As disclosed herein, such data may be provided to a third party (e.g., a health care provider). The data may be used to determine adverse events, and such events may be used to improve future programming.

Figure 5:
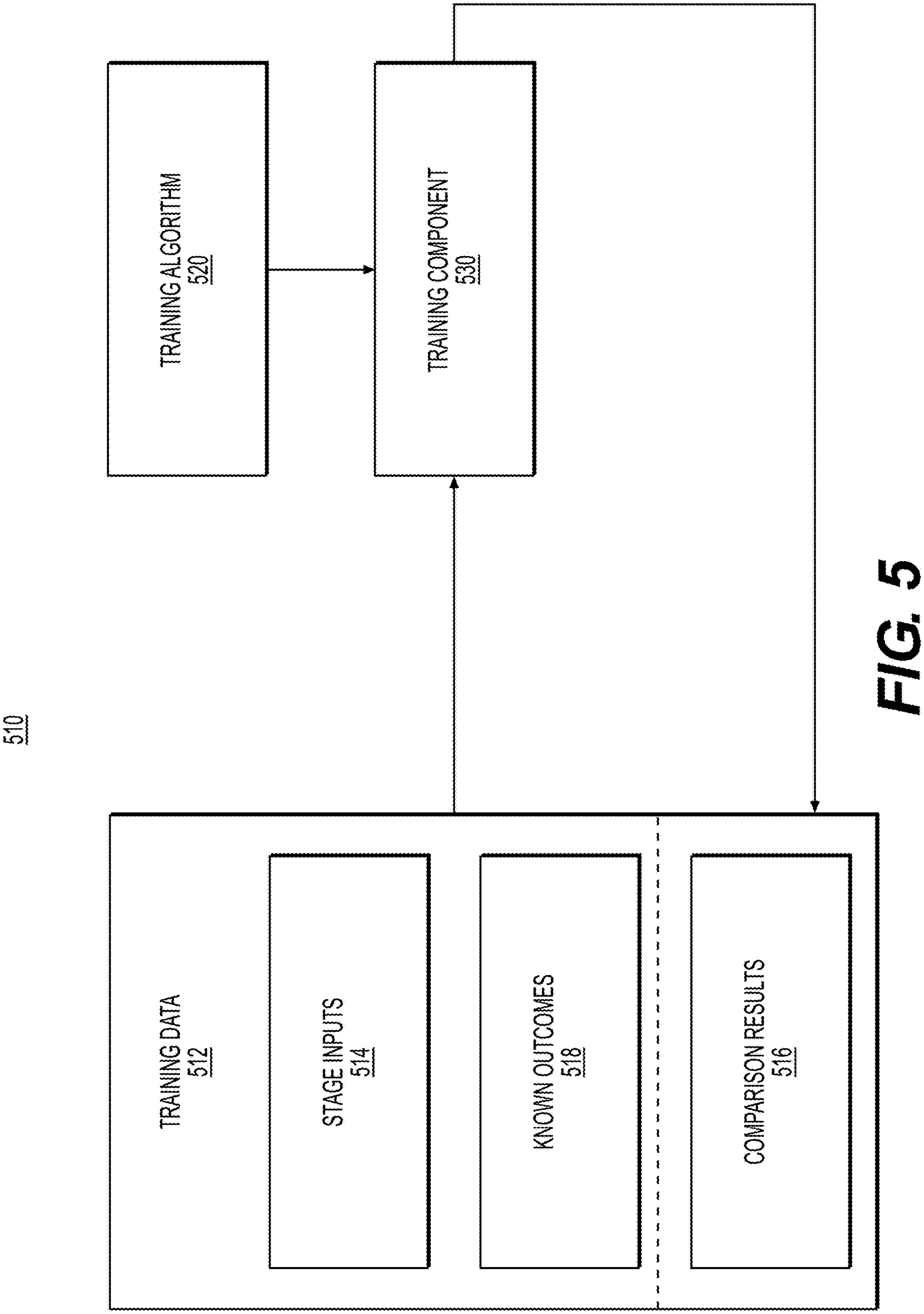
FIG. 5 depicts a machine learning model training flow, according to one or more embodiments.

One or more implementations disclosed herein may be applied by using a machine learning model. For example, a machine learning model may be used to determine a state machine and/or a next state. A machine learning model disclosed herein may be trained using the flow diagram 100 of FIG. 1A, flow diagram 130 of FIG. 1B, flow diagram 200 of FIG. 2, data flow 300 of FIG. 3, and/or flowchart 400 of FIG. 4. As shown in flow diagram 510 of FIG. 5, training data 512 may include one or more of stage inputs 514 and known outcomes 518 related to a machine learning model to be trained. The stage inputs 514 may be from any applicable source including a component or set shown in FIGS. 1A-4. The known outcomes 518 may be included for machine learning models generated based on supervised or semi-supervised training. An unsupervised machine learning model might not be trained using known outcomes 518. Known outcomes 518 may include known or desired outputs for future inputs similar to or in the same category as stage inputs 514 that do not have corresponding known outputs.

The training data 512 and a training algorithm 520 may be provided to a training component 530 that may apply the training data 512 to the training algorithm 520 to generate a machine learning model. According to an implementation, the training component 530 may be provided comparison results 516 that compare a previous output of the corresponding machine learning model to apply the previous result to re-train the machine learning model. The comparison results 516 may be used by the training component 530 to update the corresponding machine learning model. The training algorithm 520 may utilize machine learning networks and/or models including, but not limited to a deep learning network such as Deep Neural Networks (DNN), Convolutional Neural Networks (CNN), Fully Convolutional Networks (FCN) and Recurrent Neural Networks (RCN), probabilistic models such as Bayesian Networks and Graphical Models, and/or discriminative models such as Decision Forests and maximum margin methods, or the like.

In general, any process or operation discussed in this disclosure that is understood to be computer-implementable, such as the flows and/or process illustrated in FIGS. 1A-4, etc., may be performed by one or more processors of a computer system, such any of the systems or devices in the environment of FIG. 1B as described above. A process or process step performed by one or more processors may also be referred to as an operation. The one or more processors may be configured to perform such processes by having access to instructions (e.g., software or computer-readable code) that, when executed by the one or more processors, cause the one or more processors to perform the processes. The instructions may be stored in a memory of the computer system. A processor may be a central processing unit (CPU), a graphics processing unit (GPU), or any suitable types of processing unit.

Figure 6:
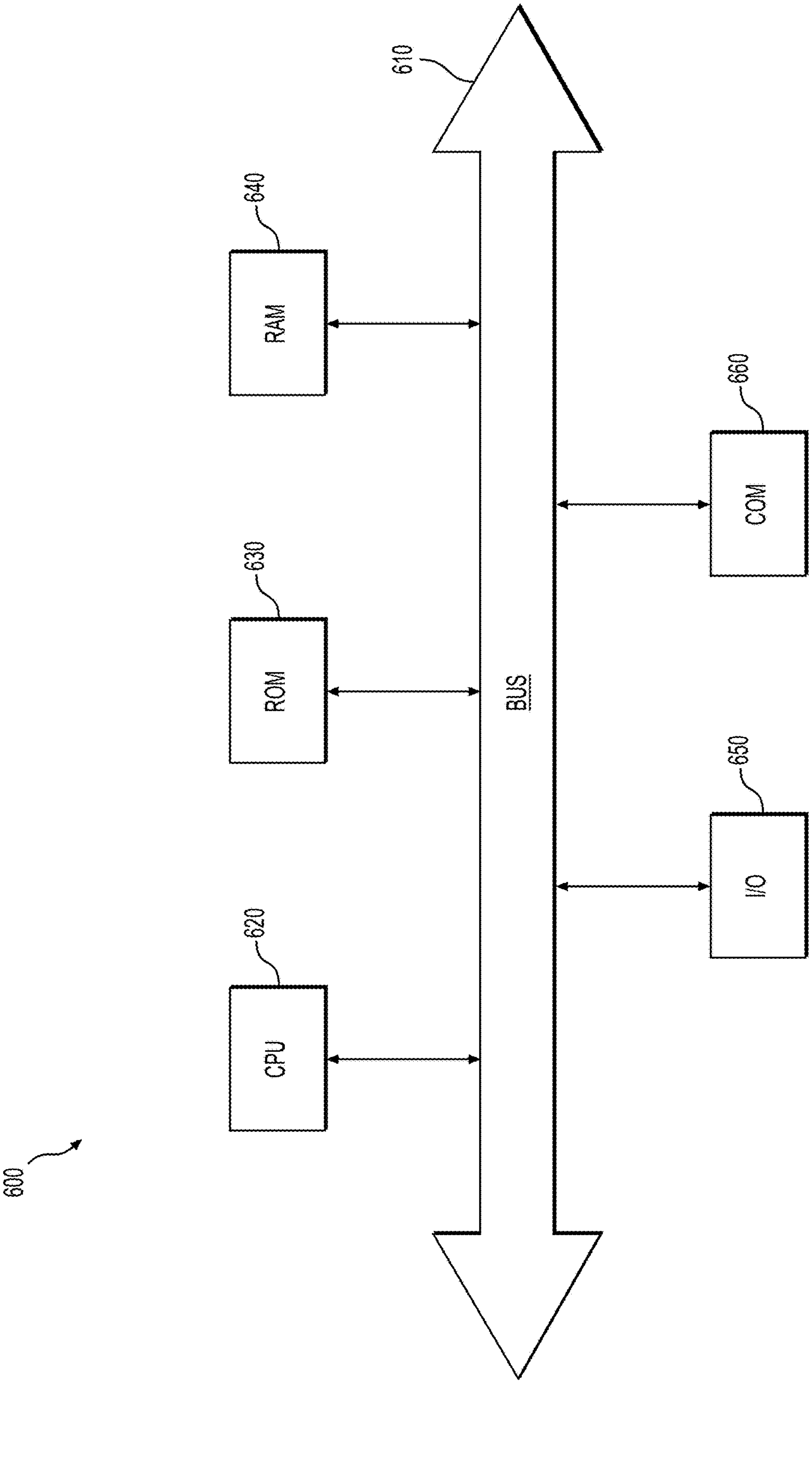
FIG. 6 depicts an example system that may execute techniques presented herein.

FIG. 6 depicts an example system 600 that may execute techniques presented herein. FIG. 6 is a simplified functional block diagram of a computer that may be configured to execute techniques described herein, according to exemplary embodiments of the present disclosure. Specifically, the computer (or "platform" as it may not be a single physical computer infrastructure) may include a data communication interface 660 for packet data communication. The platform may also include a central processing unit ("CPU") 620, in the form of one or more processors, for executing program instructions. The platform may include an internal communication bus 610, and the platform may also include a program storage and/or a data storage for various data files to be processed and/or communicated by the platform such as ROM 630 and RAM 640, although the system 600 may receive programming and data via network communications. The system 600 also may include input and output ports 650 to connect with input and output devices such as keyboards, mice, touchscreens, monitors, displays, etc. Of course, the various system functions may be implemented in a distributed fashion on a number of similar platforms, to distribute the processing load. Alternatively, the systems may be implemented by appropriate programming of one computer hardware platform.

The general discussion of this disclosure provides a brief, general description of a suitable computing environment in which the present disclosure may be implemented. In one embodiment, any of the disclosed systems, methods, and/or graphical user interfaces may be executed by or implemented by a computing system consistent with or similar to that depicted and/or explained in this disclosure. Although not required, aspects of the present disclosure are described in the context of computer-executable instructions, such as routines executed by a data processing device, e.g., a server computer, wireless device, and/or personal computer. Those skilled in the relevant art will appreciate that aspects of the present disclosure can be practiced with other communications, data processing, or computer system configurations, including: Internet appliances, hand-held devices (including personal digital assistants ("PDAs")), wearable computers, all manner of cellular or mobile phones (including Voice over IP ("VoIP") phones), dumb terminals, media players, gaming devices, virtual reality devices, multi-processor systems, microprocessor-based or programmable consumer electronics, set-top boxes, network PCs, mini-computers, mainframe computers, and the like. Indeed, the terms "computer," "server," and the like, are generally used interchangeably herein, and refer to any of the above devices and systems, as well as any data processor.

Aspects of the present disclosure may be embodied in a special purpose computer and/or data processor that is specifically programmed, configured, and/or constructed to perform one or more of the computer-executable instructions explained in detail herein. While aspects of the present disclosure, such as certain functions, are described as being performed exclusively on a single device, the present disclosure may also be practiced in distributed environments where functions or modules are shared among disparate processing devices, which are linked through a communications network, such as a Local Area Network ("LAN"), Wide Area Network ("WAN"), and/or the Internet. Similarly, techniques presented herein as involving multiple devices may be implemented in a single device. In a distributed computing environment, program modules may be located in both local and/or remote memory storage devices.

Aspects of the present disclosure may be stored and/or distributed on non-transitory computer-readable media, including magnetically or optically readable computer discs, hard-wired or preprogrammed chips (e.g., EEPROM semiconductor chips), nanotechnology memory, biological memory, or other data storage media. Alternatively, computer implemented instructions, data structures, screen displays, and other data under aspects of the present disclosure may be distributed over the Internet and/or over other networks (including wireless networks), on a propagated signal on a propagation medium (e.g., an electromagnetic wave(s), a sound wave, etc.) over a period of time, and/or they may be provided on any analog or digital network (packet switched, circuit switched, or other scheme).

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

The terminology used above may be interpreted in its broadest reasonable manner, even though it is being used in conjunction with a detailed description of certain specific examples of the present disclosure. Indeed, certain terms may even be emphasized above, however, any terminology intended to be interpreted in any restricted manner will be overtly and specifically defined as such in this Detailed Description section. Both the foregoing general description and the detailed description are exemplary and explanatory only and are not restrictive of the features, as claimed.

As used herein, the terms "comprises," "comprising," "having," including," or other variations thereof, are intended to cover a non-exclusive inclusion such that a process, method, article, or apparatus that comprises a list of elements does not include only those elements, but may include other elements not expressly listed or inherent to such a process, method, article, or apparatus.

In this disclosure, relative terms, such as, for example, "about," "substantially," "generally," and "approximately" are used to indicate a possible variation of ±10% in a stated value.

The term "exemplary" is used in the sense of "example" rather than "ideal." As used herein, the singular forms "a," "an," and "the" include plural reference unless the context dictates otherwise.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method for outputting a state machine to determine a next state for a pacemaker, the method comprising: receiving a plurality of state machines, each state machine comprising an algorithm to generate the next state for the pacemaker, wherein the next state determines a pacemaker pacing output for the pacemaker; receiving a blood pressure value sensed by a blood pressure sensor; receiving a user state; storing the blood pressure value and the user state at a user specific segment; applying an analysis module to at least one of the blood pressure value and the user state in the user specific segment; determining a subscription tier and providing data and an output of the analysis module based on the subscription tier; inputting the blood pressure value and the user state at a state machine determination module; determining a first state machine from the plurality of state machines at the state machine determination module, based on the blood pressure value and the user state; and outputting the first state machine to determine new states for the pacemaker.

2. The method of claim 1, further comprising:

receiving the pacemaker pacing output from the pacemaker;

receiving an updated blood pressure value;

receiving an updated user state; and identifying an updated state machine from the plurality of state machines based on the pacemaker pacing output, updated blood pressure value, and the updated user state.

3. The method of claim 1, further comprising:

providing the blood pressure value to the first state machine;

providing a present state to the first state machine; and receiving the next state from the first state machine, based on the blood pressure value and the present state.

4. The method of claim 3, further comprising:

receiving an updated blood pressure value;

providing the updated blood pressure value to the first state machine; and receiving a second next state from the first state machine, based on the updated blood pressure value.

5. The method of claim 1, wherein the user state is based on a heartbeat.

6. The method of claim 1, wherein the user state is one of an action or an activity.

7. The method of claim 1, further comprising receiving a heartbeat value and determining the first state machine further based on the heartbeat value.

8. The method of claim 1, further comprising:

receiving a subjective input;

providing the subjective input to the first state machine; and receiving the next state from the first state machine further based on the subjective input.

9. The method of claim 1, wherein the first state machine is determined based on at least one of a chronic trigger or an event trigger.

10. The method of claim 1, wherein the next state is generated based on at least one of a chronic trigger or an event trigger.

11. The method of claim 1, further comprising receiving historical state outputs and determining the first state machine further based on the historical state outputs.

12. The method of claim 1, further comprising triggering a safeguard, the safeguard comprising a kill switch function that causes the pacemaker to abort the new states.

13. The method of claim 12, wherein the safeguard is based on one of the blood pressure value, the user state, or a user experience.

14. A system comprising: a state machine determination module; a pacemaker; a pacing output module; and a processor in communication with the state machine determination module, the pacemaker, and the pacing output module, the processor configured to: receive a plurality of state machines, each state machine comprising an algorithm to generate a next state for the pacemaker, wherein the next state determines a pacemaker pacing output for the pacemaker; receive a blood pressure value sensed by a blood pressure sensor; receive a user state; store the blood pressure value and the user state at a user specific segment; apply an analysis module to at least one of the blood pressure value and the user state in the user specific segment; determine a subscription tier and providing data and an output of the analysis module based on the subscription tier; input the blood pressure value and the user state at the state machine determination module; determine a first state machine from the plurality of state machines at the state machine determination module, based on the blood pressure value and the user state; provide the first state machine to the pacing output module; receive a next state from the pacing output module based on the first state machine and the blood pressure value, wherein the next state determines a pacemaker pacing output for the pacemaker; and provide the next state to the pacemaker.

15. The system of claim 14, wherein the processor is a remote processor in communication with the state machine determination module, the pacemaker, and the pacing output module over a network.

16. A method for outputting a state machine to determine a next state for a pacemaker, the method comprising: receiving a plurality of state machines, each state machine comprising an algorithm to generate the next state for the pacemaker, wherein the next state determines a pacemaker pacing output for the pacemaker; receiving a physiological input value sensed by a sensor; receiving a user state; storing the physiological input value and the user state at a user specific segment; applying an analysis module to at least one of the physiological input value and the user state in the user specific segment; determining a subscription tier and providing data and an output of the analysis module based on the subscription tier; inputting the physiological input value at a state machine determination module; determining a first state machine from the plurality of state machines at the state machine determination module, based on the physiological input value; outputting the first state machine to determine new states for the pacemaker; providing the physiological input value to the first state machine; providing a present state to the first state machine; and receive the next state from the first state machine, based on the physiological input value and the present state.

17. The method of claim 16, further comprising configuring the pacemaker to output the pacemaker pacing output based on the next state.

* * * * *